United States Patent
Ramstad et al.

(10) Patent No.: US 11,457,989 B2
(45) Date of Patent: Oct. 4, 2022

(54) SURGICAL DRAPE INSTALLATION AID (71) Applicant: INTUITIVE SURGICAL OPERATIONS, INC., Sunnyvale, CA (US)

(72) Inventors: Craig R. Ramstad, Minden, NV (US); Robert E. Holop, Santa Clara, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 843 days.

(21) Appl. No.: 16/317,289

(22) PCT Filed: May 25, 2017

(86) PCT No.: PCT/US2017/034453
§ 371 (c)(1),
(2) Date: Jan. 11, 2019

(87) PCT Pub. No.: WO2018/013236
PCT Pub. Date: Jan. 18, 2018

(65) Prior Publication Data
US 2019/0298470 A1      Oct. 3, 2019

Related U.S. Application Data

(60) Provisional application No. 62/362,190, filed on Jul. 14, 2016.

(51) Int. Cl.
*A61B 46/10* (2016.01)
*A61B 34/37* (2016.01)
(Continued)

(52) U.S. Cl.
CPC .............. *A61B 46/10* (2016.02); *A61B 34/37* (2016.02); *A61B 46/00* (2016.02); *A61B 90/37* (2016.02); *A61B 2017/00477* (2013.01)

(58) Field of Classification Search
CPC combination set(s) only.
See application file for complete search history.

(56) References Cited

U.S. PATENT DOCUMENTS

| | | |
|---|---|---|
| 3,968,792 A | 7/1976 | Small |
| 2004/0035334 A1 | 2/2004 | Lohrengel et al. |

(Continued)

FOREIGN PATENT DOCUMENTS

| | | |
|---|---|---|
| CN | 102626344 A | 8/2012 |
| CN | 102711652 A | 10/2012 |

(Continued)

OTHER PUBLICATIONS

Office Action dated Jun. 18, 2021 for Chinese Application No. 201780048276.9 filed May 25, 2017, 24 pages.

(Continued)

*Primary Examiner* — Scott Luan
(74) *Attorney, Agent, or Firm* — Jones Robb, PLLC (57) ABSTRACT

A surgical drape installation aid comprises a body comprising a sidewall and a plurality of rotatable seal interface elements. The sidewall bounds an interior volume of the body and has a first end and a second end. The first end of the sidewall bounds a first open end of the body and the second end of the sidewall bounds a second open end of the body. Each of the plurality of rotatable seal interface elements extends from the second end of the sidewall.

20 Claims, 7 Drawing Sheets (51) Int. Cl.
*A61B 90/00* (2016.01)
*A61B 46/00* (2016.01)
*A61B 17/00* (2006.01)

(56) References Cited

U.S. PATENT DOCUMENTS

| | | |
|---|---|---|
| 2004/0156100 A1 | 8/2004 | Fuchs et al. |
| 2011/0277775 A1 | 11/2011 | Holop et al. |
| 2014/0188001 A1 | 7/2014 | Miller et al. |
| 2015/0202009 A1 | 7/2015 | Nussbaumer et al. |

FOREIGN PATENT DOCUMENTS

| | | |
|---|---|---|
| JP | 2016064449 A | 4/2016 |
| KR | 20080085143 A | 9/2008 |
| KR | 20110057108 A | 5/2011 |
| KR | 20170107587 A | 9/2017 |
| WO | WO-2007041093 A1 | 4/2007 |
| WO | WO-2011090633 A2 | 7/2011 |
| WO | WO-2018013236 A1 | 1/2018 |

OTHER PUBLICATIONS

Office Action dated Dec. 20, 2021 for Chinese Application No. CN201780048276.9 filed May 25, 2017 with English Translation, 12 pages.
Extended European Search Report for Application No. EP17828118.4, dated Jan. 30, 2020, 9 pages.
International Search Report and Written Opinion for Application No. PCT/US2017/034453, dated Sep. 8, 2017, 15 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

SURGICAL DRAPE INSTALLATION AID

RELATED APPLICATIONS

This patent application is a U.S. national stage application under 35 U.S.C. § 371(c) of International Application No. PCT/US2017/034453, filed on May 25, 2017, which claims priority to and the filing date benefit of U.S. Provisional Patent Application No. 62/362,190, entitled "SURGICAL DRAPE INSTALLATION AID" filed Jul. 14, 2016, each of which is incorporated by reference herein in their entirety.

BACKGROUND

Field of the Invention

The present invention relates generally to sterile drapes for computer-assisted surgical systems, and more particularly to apparatus used in sterile drape installation.

Description of Related Art

In computer-assisted telerobotic surgery, a surgeon typically operates a master controller to control motion of surgical instruments at the surgical site from a location that may be remote from the patient (e.g., across the operating room, in a different room or in a completely different building from the patient). The master controller usually includes one or more input devices, which are coupled to the surgical instruments with servo motors for articulating the instruments at the surgical site. The servo motors are typically part of an electromechanical device or surgical manipulator ("the slave") that supports and controls the surgical instruments that have been introduced directly into an open surgical site or through trocar sleeves into a body cavity, such as the patient's abdomen. During the operation, the surgical manipulator provides mechanical articulation and control of a variety of surgical instruments, such as tissue graspers, needle drivers, electrosurgical cautery probes, etc., that each performs various functions for the surgeon, e.g., holding or driving a needle, grasping a blood vessel, or dissecting, cauterizing or coagulating tissue.

Computer-assisted surgery through remote manipulation reduces the size and number of incisions required in surgery to enhance patient recovery while also helping to reduce patient trauma and discomfort. However, computer-assisted surgery has also created many new challenges.

One challenge is that a portion of an electromechanical surgical manipulator is positioned adjacent to the surgical site. The surgical manipulator may become contaminated during surgery and is typically disposed of or sterilized between uses. From a cost perspective, it would be preferable to sterilize the device. However, the servo motors, sensors, encoders, and electrical connections that are necessary to robotically control the motors typically cannot be sterilized using conventional methods, e.g., steam, heat and pressure, or chemicals, because the system parts would be damaged or destroyed in the sterilization process.

A sterile drape has been previously used to cover the surgical manipulator. The drapes have taken various forms. In each instance, the surgical manipulator and support links are covered with a drape prior to the start of the surgical procedure. Unfortunately, a patient side support system used in computer assisted surgery is a large item, and the size makes it difficult to cover the necessary parts of the patient side support system without compromising the sterility of the drape and without compromising the drape's integrity.

SUMMARY

In one aspect, a surgical drape installation aid includes a body comprising a sidewall and a plurality of rotatable seal interface elements. The sidewall has a first end and a second end. The first end of the sidewall bounds a first open end of the body, while the second end of the sidewall bounds a second open end of the body. Each of the plurality of rotatable seal interface elements extends from the second end of the sidewall. The sidewall bounds an interior volume of the body.

The surgical drape installation aid also includes a bag having an open end. The open end of the bag is fixedly attached to a first surface, e.g., an interior side surface, of the sidewall between the first end of the sidewall and the second end of the sidewall. The bag is configured to extend from the first end of the sidewall.

In one aspect, the surgical drape installation aid further includes a plurality of surgical drape management features. Each of the plurality of surgical drape management features is configured to hold a portion of the surgical drape against a second surface of the sidewall, e.g., an exterior side surface. The first surface of the sidewall and the second surface of the sidewall are different surfaces. The plurality of surgical drape management features includes a clamp attachable to the sidewall. The surgical drape installation aid yet still includes a sterile adapter retaining device.

A system includes a surgical drape and a surgical drape installation aid. The surgical drape includes a first portion and a second portion. The surgical drape installation aid includes a body having a sidewall. The sidewall has a first end, a second end, an interior side surface, and an exterior side surface. The exterior side surface extends between the first end and the second end. The interior side surface extends between the first end and the second end. The first end of the sidewall bounds a first open end of the body, while the second end of the sidewall bounds a second open end of the body. The interior side surface of the sidewall bounds an interior volume of the body.

The second portion of the surgical drape is positioned in the interior volume of the body. At least part of the first portion of the surgical drape is mounted on the exterior side surface of the body.

In one aspect of the system, the surgical drape also includes an optional rotatable seal comprising a stationary seal portion and a rotatable seal portion. The rotatable seal portion is configured to rotate relative to the stationary seal portion. The first portion of the surgical drape is affixed to the stationary seal portion, and the second portion of the surgical drape is affixed to the rotatable seal portion. The surgical drape installation aid further includes a plurality of rotatable seal interface elements. Each of the plurality of rotatable seal interface elements extends from the second end of the sidewall. The rotatable seal interface elements are engaged with the rotatable seal.

In another aspect of the system, the surgical drape installation aid includes an optional bag having an open end. The open end of the bag is fixedly attached to the interior side surface of the sidewall between the first end of the sidewall and the second end of the sidewall. The bag is configured to extend from the first end of the sidewall.

In another aspect of the system, the surgical drape installation aid includes a plurality of surgical drape management features. Each of the plurality of surgical drape management features is configured to hold the part of the first portion of the surgical drape against the exterior side surface of the sidewall. In one aspect, the plurality of surgical drape management features includes a clamp attachable to the sidewall. The surgical drape installation aid in this system also includes a sterile adapter retaining device.

A method includes placing a second portion of a surgical drape in an interior volume of a body. The body includes a sidewall. The sidewall has a first end, a second end, an interior side surface, and an exterior side surface. The exterior side surface extends between the first end and the second end. The interior side surface extends between the first end and the second end. The first end of the sidewall bounds a first open end of the body, while the second end of the sidewall bounds a second open end of the body. The interior side surface of the sidewall bounds the interior volume of the body. The method also includes mounting a first portion of the surgical drape on the exterior side surface of the body.

In one aspect, the first portion and the second portion of the surgical drape are attached to an optional rotatable seal. The mounting the second portion then includes mounting the rotatable seal on a plurality of rotatable seal interface elements, each of the plurality of rotatable seal interface elements extending from the second end of the sidewall.

BRIEF DESCRIPTION OF THE DRAWINGS

In the drawings, the first digit in a single digit reference numeral of an element is the number of the figure in which that element first appears.

DETAILED DESCRIPTION

In one aspect, a surgical drape installation package 170 (FIG. 1) includes a surgical drape installation aid 150 with a surgical drape 160 packaged in surgical drape installation aid 150. At least a portion of surgical drape 160 is sterile.

Figure 1:
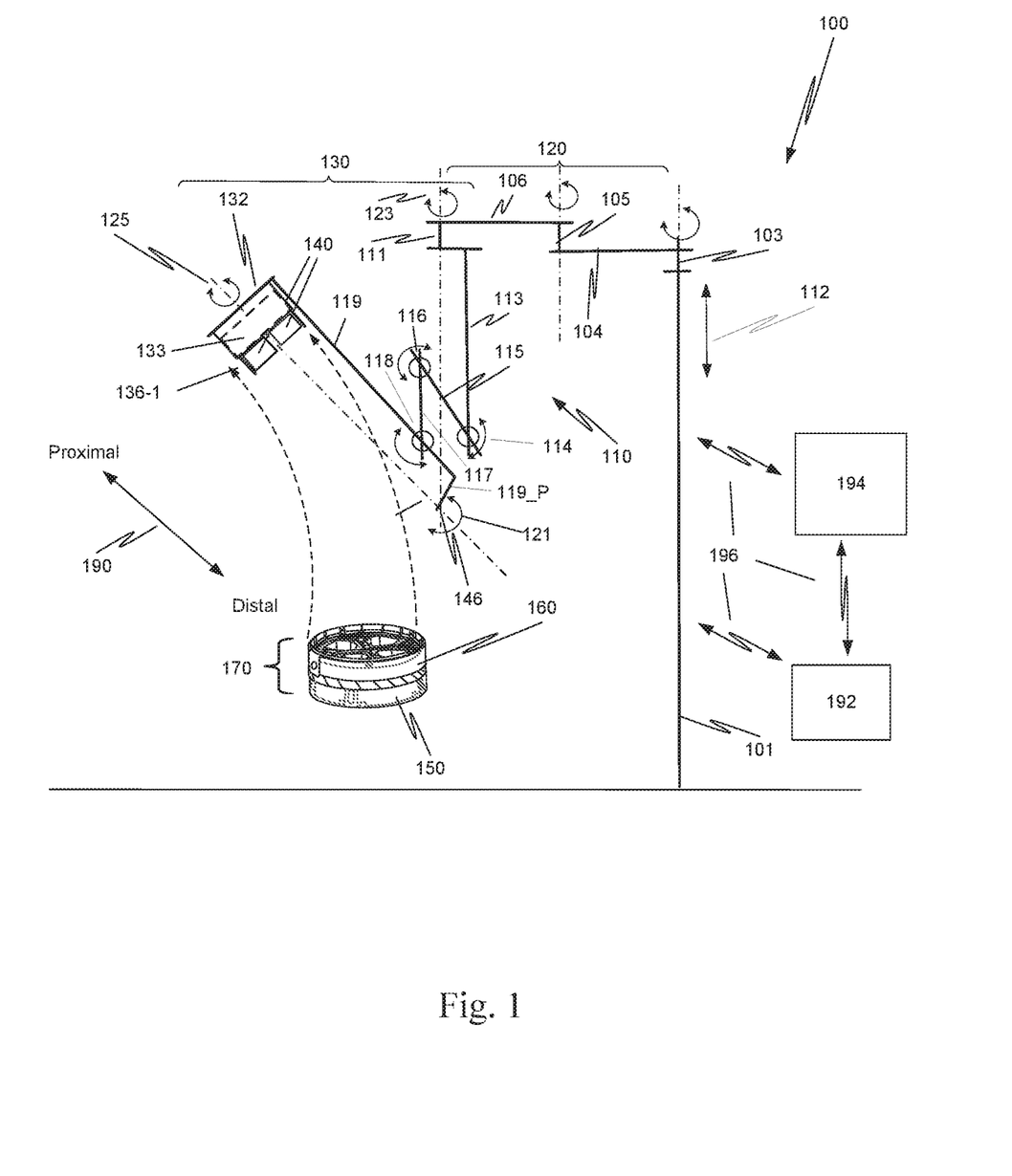
FIG. 1 is an illustration of a computer-assisted surgical system with a surgical drape installation package that includes a sterile surgical drape and a surgical drape installation aid.

Surgical drape installation package 170 is used to facilitate positioning surgical drape 160 on a computer-assisted surgical system 100 without contaminating the sterility of sterile portions of surgical drape 160 and without compromising the integrity of surgical drape 160. In one aspect, surgical drape 160 includes manipulator assembly boots and sterile adapters that are packaged in surgical drape installation aid 150.

Surgical drape installation package 170, sometimes referred to as package 170, facilitates easily grasping packaged surgical drape 160, which is large and bulky, and facilitates intuitively mounting package 170 on computer-assisted surgical system 100 so that the draping process can be performed. Since surgical drape 160 is sterilized after being positioned in surgical drape installation aid 150, use of surgical drape installation aid 150 does not compromise sterility, and instead helps assure that sterile parts of surgical drape 160 do not come into contact with non-sterile surfaces or objects as surgical drape 160 is initially being affixed to computer-assisted surgical system 100, sometimes referred to as surgical system 100.

Further, features of surgical drape installation aid 150 assure that features of surgical drape 160 are properly aligned with corresponding features of patient side support system 110 as package 170 is mounted on computer-assisted surgical system 100. The automatic alignment of the features means that the features do not have to be manually aligned, and so speeds up the draping process in comparison to a draping process that required the manual alignment of these features.

Surgical drape 160 includes a first portion and a second portion. Surgical drape installation aid 150 includes a body having a sidewall. The sidewall has a first end, a second end, an interior side surface, and an exterior side surface. The exterior side surface extends between the first end and the second end. The interior side surface also extends between the first end and the second end. The first end of the sidewall bounds a first open end of the body, while the second end of the sidewall bounds a second open end of the body. The interior side surface of the sidewall bounds an interior volume of the body.

The second portion of surgical drape 160 is positioned in the interior volume of the body of surgical drape installation aid 150. At least part of the first portion of the surgical drape 160 is mounted on the exterior side surface of the body.

In one aspect, surgical drape 160 also includes an optional rotatable seal, which has a stationary seal portion and a rotatable seal portion. The rotatable seal portion is configured to rotate relative to the stationary seal portion. The first portion of the surgical drape is affixed to the stationary seal portion, and the second portion of the surgical drape is affixed to the rotatable seal portion. In this aspect, surgical drape installation aid 150 includes an optional plurality of rotatable seal interface elements. Each of the plurality of rotatable seal interface elements extends from the second end of the sidewall. The rotatable seal interface elements are engaged with the rotatable seal and assure that all parts of the rotatable seal are aligned to mate with corresponding parts on patient side support system 110.

In another aspect, surgical drape installation aid 150 includes an optional bag having an open end. The open end of the bag is fixedly attached to the interior side surface of the sidewall between the first end of the sidewall and the second end of the sidewall. The bag is configured to extend from the first end of the sidewall.

The surgical drape installation aid 150 includes a plurality of surgical drape management features. Each of the plurality of surgical drape management features is configured to hold the part of the first portion of surgical drape 160 against the exterior side surface of the sidewall. In one aspect, the plurality of surgical drape management features includes a clamp attachable to the sidewall.

A method includes placing a second portion of surgical drape 160 in an interior volume of a body of surgical drape installation aid 150. The body includes a sidewall. The sidewall has a first end, a second end, an interior side surface, and an exterior side surface. The exterior side surface extends between the first end and the second end. The interior side surface extends between the first end and the second end. The first end of the sidewall bounds a first open end of the body, while the second end of the sidewall bounds a second open end of the body. The interior side surface of the sidewall bounds the interior volume of the body. The method also includes mounting a first portion of surgical drape 160 on the exterior side surface of the body.

In one aspect, the first portion and the second portion of surgical drape 160 are attached to an optional rotatable seal. The mounting the second portion then includes mounting the rotatable seal on an optional plurality of rotatable seal interface elements, each of the plurality of rotatable seal interface elements extending from the second end of the sidewall.

In this aspect, surgical system 100 includes an endoscopic imaging system 192, a surgeon's console 194 (master), and a patient side support system 110 (slave), all interconnected by wired (electrical or optical) or wireless connections 196. One or more electronic data processors may be variously located in these main components to provide system functionality. Examples are disclosed in U.S. Pat. No. 9,060,678, which is incorporated by reference herein.

Imaging system 192 performs image processing functions on, e.g., captured endoscopic imaging data of the surgical site and/or preoperative or real time image data from other imaging systems external to the patient. Imaging system 192 outputs processed image data (e.g., images of the surgical site, as well as relevant control and patient information) to a surgeon at surgeon's console 194. In some aspects, the processed image data is output to an optional external monitor visible to other operating room personnel or to one or more locations remote from the operating room (e.g., a surgeon at another location may monitor the video; live feed video may be used for training; etc.).

Surgeon's console 194 includes multiple degrees-of-freedom ("DOF") mechanical input devices ("masters") that allow the surgeon to manipulate the instruments, entry guide(s), and imaging system devices, which are collectively referred to as slaves. These input devices may in some aspects provide haptic feedback from the instruments and surgical device assembly components to the surgeon. Console 194 also includes a stereoscopic video output display positioned such that images on the display are generally focused at a distance that corresponds to the surgeon's hands working behind/below the display screen. These aspects are discussed more fully in U.S. Pat. No. 6,671,581, which is incorporated by reference herein.

Control during insertion of the instruments may be accomplished, for example, by the surgeon moving the instruments presented in the image with one or both of the masters; the surgeon uses the masters to move the instrument in the image side to side and to pull the instrument towards the surgeon. The motion of the masters commands the imaging system and an associated surgical device assembly to steer towards a fixed center point on the output display and to advance inside the patient.

In one aspect, the camera control is designed to give the impression that the masters are fixed to the image so that the image moves in the same direction that the master handles are moved. This design causes the masters to be in the correct location to control the instruments when the surgeon exits from camera control, and consequently this design avoids the need to clutch (disengage), move, and declutch (engage) the masters back into position prior to beginning or resuming instrument control.

Base 101 of patient side support system 110 supports an arm assembly that includes a passive, uncontrolled setup arm assembly 120 and an actively controlled manipulator arm assembly 130. Actively controlled manipulator arm assembly 130 is referred to as entry guide manipulator 130.

In one example, the setup portion includes and two passive rotational setup joints 103 and 105. Rotational setup joints 103 and 105 allow manual positioning of the coupled setup links 104 and 106 if the joint brakes for setup joints 103 and 105 are released. Alternatively, some of these setup joints may be actively controlled, and more or fewer setup joints may be used in various configurations. Setup joints 103 and 105 and setup links 104 and 106 allow a person to place entry guide manipulator 130 at various positions and orientations in Cartesian x, y, z space. A prismatic setup joint (not shown) between link 104 of arm assembly 120 and base 101 may be used for vertical adjustments 112.

A remote center of motion 146 is a location at which yaw, pitch, and roll axes intersect (i.e., the location at which the kinematic chain remains effectively stationary while joints move through their range of motion). Some of these actively controlled joints are manipulators that are associated with controlling DOFs of individual instruments, and others of these actively controlled joints are associated with controlling DOFs of a single assembly of these manipulators. The active joints and links are movable by motors or other actuators and receive movement control signals that are associated with master arm movements at surgeon's console 194.

As shown in FIG. 1, a manipulator assembly yaw joint 111 is coupled between an end of setup link 106 and a second end, e.g., a proximal end, of a first manipulator link 113. Yaw joint 111 allows first manipulator link 113 to move with reference to link 106 in a motion that may be arbitrarily defined as "yaw" around a manipulator assembly yaw axis 123. As shown, the rotational axis of yaw joint 111 is aligned with a remote center of motion 146, which is generally the position at which an instrument enters the patient (e.g., at the umbilicus for abdominal surgery).

In one embodiment, setup link 106 is rotatable in a horizontal or x, y plane and yaw joint 111 is configured to allow first manipulator link 113 in entry guide manipulator 130 to rotate about yaw axis 123. Setup link 106, yaw joint 111, and first manipulator link 113 provide a constantly vertical yaw axis 123 for entry guide manipulator 130, as illustrated by the vertical line through yaw joint 111 to remote center of motion 146.

A distal end of first manipulator link 113 is coupled to a proximal end of a second manipulator link 115 by a first actively controlled rotational joint 114. A distal end of second manipulator link 115 is coupled to a proximal end of a third manipulator link 117 by a second actively controlled rotational joint 116. A distal end of third manipulator link 117 is coupled to a distal portion of a fourth manipulator link 119 by a third actively controlled rotational joint 118.

In one embodiment, links 115, 117, and 119 are coupled together to act as a coupled motion mechanism. Coupled motion mechanisms are well known (e.g., such mechanisms are known as parallel motion linkages when input and output link motions are kept parallel to each other). For example, if rotational joint 114 was actively rotated, joints 116 and 118 are also actively rotated so that link 119 moves with a constant relationship to link 115. Therefore, it can be seen that the rotational axes of joints 114, 116, and 118 are parallel. When these axes are perpendicular to rotational axis 123 of joint 111, links 115, 117, and 119 move with reference to link 113 in a motion that may be arbitrarily defined as "pitch" around a manipulator assembly pitch axis. The manipulator pitch axis extends into and out of the page in FIG. 1 at remote center of motion 146, in this aspect. The motion around the manipulator assembly pitch axis is represented by arrow 121. Since links 115, 117, and 119 move as a single assembly in this embodiment, first manipulator link 113 may be considered an active proximal manipulator link, and second through fourth manipulator links 115, 117, and 119 may be considered collectively an active distal manipulator link.

An entry guide manipulator assembly platform 132, sometimes referred to as platform 132, is coupled to a distal end of fourth manipulator link 119. An entry guide manipulator assembly 133 is rotatably mounted on platform 132. Entry guide manipulator assembly 133 includes an instrument manipulator positioning system.

Entry guide manipulator assembly 133 rotates plurality of surgical instrument manipulator assemblies 140 as a group around axis 125. Specifically, entry guide manipulator assembly 133 rotates as a single unit with reference to platform 132 in a motion that may be arbitrarily defined as "roll" around an entry guide manipulator assembly roll axis 125.

Each of a plurality of surgical instrument manipulator assemblies 140 is coupled to entry guide manipulator assembly 133 by a different insertion assembly 136-1. In one aspect, each insertion assembly 136-1 is a telescoping assembly that moves the corresponding instrument manipulator assembly away from and towards entry guide manipulator assembly 133. In FIG. 1, each of the insertion assemblies is in a retracted position.

Each of the plurality of instrument manipulator assemblies 140 includes a plurality of motors that drive a plurality of outputs in an output interface of that instrument manipulator assembly. See U.S. Patent Application Publication No. US 2016-0184037 A1 (filed on 11 Feb. 2016), which is incorporated by reference, for one example of a surgical instrument manipulator assembly and a surgical instrument that can be coupled to the surgical instrument manipulator assembly.

In one aspect, a membrane interface that is part of a sterile surgical drape may be placed between the instrument mount interface of an instrument manipulator assembly and the input interface of the transmission unit of a corresponding surgical instrument. See, for example, U.S. Patent Application Publication No. US 2011/0277776 A1 for an example of the membrane interface and sterile surgical drape. In another aspect, a sterile adapter that is part of a sterile surgical drape may be placed between the instrument mount interface of the instrument manipulator assembly and the input interface of the transmission unit of the corresponding surgical instrument. See, for example, U.S. Patent Application Publication No. US 2011/0277775 A1 for an example of a sterile adapter and a sterile surgical drape. Surgical drape 160 is configured to cover at least entry guide manipulator 130. When surgical drape 160 is fully deployed on entry guide manipulator 130, surgical drape 160 shields non-sterile parts of entry guide manipulator 130 from the sterile field, and also shields entry guide manipulator 130 from materials from the surgical procedure (e.g., body fluids, etc.).

In one embodiment, surgical drape 160 includes a first portion 261 (FIG. 2) configured to shield platform 132, links 113, 115, 117, and 119, and the associated joints. First portion 261 includes an exterior sterile surface and an interior surface. The interior surface is configured to be positioned adjacent to platform 132, links 113, 115, 117, and 119, and the associated joints. First portion 261 is affixed to a stationary portion of rotatable seal 265, such as a roll cover portion of a rotatable labyrinth seal.

Figure 2:
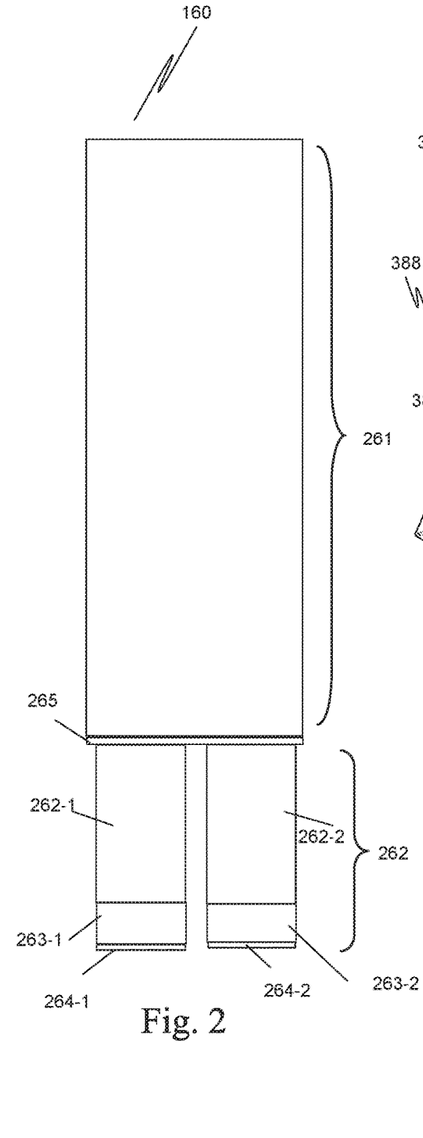
FIG. 2 is a representation of one example of a surgical drape.

A second portion 262 of surgical drape 160 includes a plurality of drape sleeves 262-1 to 262-4 (drape sleeves 262-3, and 262-4 are not visible in FIG. 2), with each drape sleeve including at a distal end a boot and a sterile adapter—only boots 263-1, 263-2 and sterile adapter 264-1, 264-2 are visible in FIG. 2. Each sterile adapter includes a mechanical interface configured to mate between the instrument mount interface of a respective surgical instrument manipulator assembly and the input interface of the transmission unit of the corresponding surgical instrument.

A rotating portion of rotatable seal 265, such as a base comb portion of a rotating labyrinth seal, is coupled to a proximal opening of each of plurality of drape sleeves 262-1 to 262-4 to allow all of the drape sleeves to rotate together as a group with reference to more proximal first portion 261 of surgical drape 160. See U.S. Patent Application Publication No. US 2011/0277775 A1 for an example of a suitable surgical drape and rotatable seal.

In one aspect, first portion of 261 of surgical drape 160 and the plurality of drape sleeves are made of a polyethylene material such as ethylene methyl acrylate, commonly referred to as "EMA." In one aspect, each of the plurality of boots is made from low-density polyethylene (LDPE).

As explained more completely below, second portion 262 of surgical drape 160 is placed in an interior space of surgical drape installation aid 150. Rotatable seal 265 is mounted on surgical drape installation aid 150. First portion 261 of surgical drape 160 is then accordion folded and attached to an outer surface of surgical drape installation aid 150. Packaging surgical drape 160 in this way in surgical drape installation aid 150 allows a person to easily grasp surgical drape installation aid 150 with surgical drape 160 attached.

A person grasps surgical drape installation aid 150 with the packaged surgical drape 160 and moves the package around entry guide manipulator assembly 133 and plurality of surgical instrument manipulator assemblies 140 (see dotted lines in FIG. 1 showing one possible range of motion) and uses alignment features on the stationary portion of rotatable seal 265 to position the package so that each of the latches on the stationary portion of rotatable seal 265 engage a corresponding latch receptacle in platform 132.

As surgical drape installation package 170 is mounted on system 100, the second portion of the surgical drape may fall below the bottom edge of the body of surgical drape installation aid 150. However, a bag is attached to the interior of the body of surgical drape installation aid 150 to prevent the second portion from contacting any non-sterile object and to limit the downward movement so that surgical drape installation package is still easily mounted on system 100.

Figure 3:
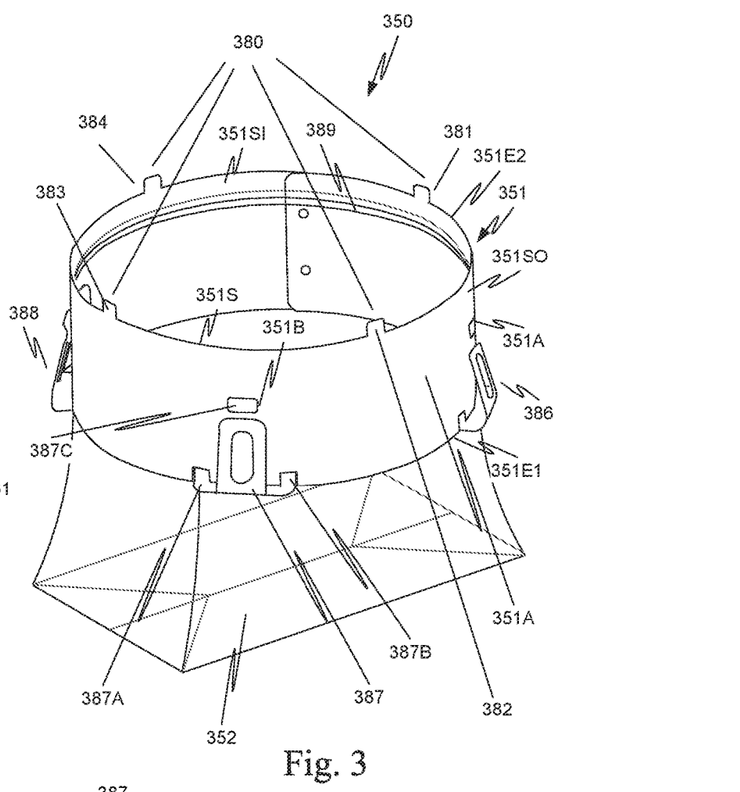
FIG. 3 illustrates one aspect of the surgical drape installation aid.

FIG. 3 is an oblique view of a surgical drape installation aide 350. Surgical drape installation aid 350 is one example of surgical drape installation aid 150.

Surgical drape installation aide 350 includes a body 351, which is sometimes referred to as a collar. Body 351 includes a sidewall 351S and a plurality of rotatable seal interface elements 380. If a surgical drape does not include a rotatable seal, plurality of rotatable seal interface elements 380 may not be needed, and so are said to be optional.

Sidewall 351S has a first end 351E1 and a second end 351E2. Second end 351E2 is different from and removed from first end 351E1. First end 351E1 bounds a first open end of body 351, while second end 351E2 bounds a second open end of body 351.

Sidewall 351S has an inner sidewall surface 351SI bounding an interior volume of body 351 and an outer sidewall surface 351SO (also called "outer surface 351SO"). Each of plurality of rotatable seal interface elements 380 extend from second end 351E2 of sidewall 351S in a direction away from both first end 351E1 and second end 351E2.

In one aspect, body 351 is made of a strip of high density polyethylene (HDPE). The strip of high density polyethylene (HDPE) is formed into an open cylindrical shape, and then a lap joint is made and ultrasonically welded to form body 351 shown in FIG. 3. The use of a cylindrically shaped body is illustrative only is not intended to be limiting. The shape of the body of surgical drape installation aid 350 is selected to support the surgical drape and to facilitate attaching the surgical drape to the surgical system.

The use of HDPE also is illustrative only and is not intended to be limiting. Any material can be used to make body 351, which is lightweight, and which is rigid enough to support the surgical drape and rigid enough to allow manipulation of the resulting drape installation package 170 without deformation that could lead to inadvertent contact of the surgical drape with a non-sterile object in the process of mounting surgical drape installation package 170 on the surgical system.

In this embodiment, plurality of rotatable seal interface elements 380, sometimes referred to as plurality 380, includes four rotatable seal interface elements 381, 382, 383, and 384. Each of plurality of rotatable seal interface elements 380 is sometimes referred to as a tab or is referred to as a castellation.

In one aspect, the number of rotatable seal interface element in plurality 380 is determined by the number of attachment elements, e.g., latches, of rotatable seal 265 that are used to attach rotatable seal 265 to platform 132. In this aspect, the stationary portion of rotatable seal 265 includes four latches, and so body 351 includes four rotatable seal interface elements 381, 382, 383, and 384. This number of rotatable seal interface elements is illustrative only and is not intended to be limiting. In other aspects, the number of rotatable seal interface elements in plurality 380 can be either smaller than the number of attachment elements of rotatable seal 265 or larger than the number of the number of attachment elements of rotatable seal 265.

Figure 6:
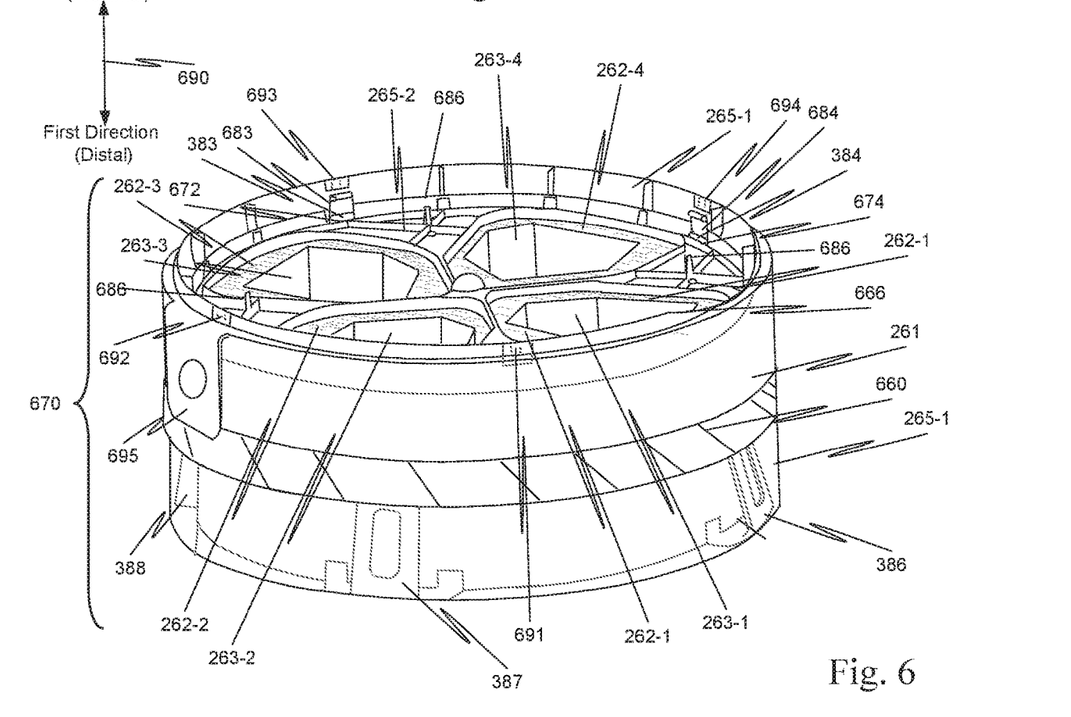
FIG. 6 is an illustration a surgical drape installation package including the surgical drape installation aid of FIG. 3 with the surgical drape of FIG. 2 mounted in the surgical drape installation aid.

Plurality of rotatable seal interface elements 380 holds surgical drape installation package 670 (FIG. 6) in place until first portion 261 of drape 160 is deployed, for example, around links 113, 115, 117, and 119 and the associated joints. Surgical drape installation aid 350 is held in place, in one aspect, by friction between plurality of rotatable seal interface elements 380 and the two portions of rotatable seal 265. Alternatively, surgical drape installation aid 350 could be held in place with a feature that locked to an element or elements of the sterile surgical drape. In FIG. 6, the proximal and distal directions are represented by arrow 690.

Accordingly, the number of rotatable seal interface elements in plurality of rotatable seal interface elements 380 can be varied so long as there is sufficient friction between plurality of rotatable seal interface elements 380 and rotatable seal 265 so that drape installation aid 350 and the attached portions of packaged drape 160 do not disengage from rotatable seal 265 until the person draping system 100 pulls drape installation aid 350 out of rotatable seal 265.

Typically, drape installation aid 350 is removed after first portion 261 of drape 160 is deployed, and the user is ready to deploy second portion 262 of drape 160. However, drape installation aid 350 could also be removed before first portion 261 of drape 160 is deployed, or perhaps while first portion 261 of drape 160 is deployed.

Surgical drape installation aid 350 also includes a plurality of drape management features, e.g., drape management features 386, 387, and 388. In this example, drape management features 386, 387, and 388 are clamps which are attached to sidewall 351S about the edge comprising first end 351E1. Thus, in this example, drape management features 386, 387, 388 may also be called clamps 386, 387, 388. In this example, body 351 of surgical drape installation aid 350 includes a plurality of drape management alignment elements, e.g., through openings 351A, 351B, and 351C (not visible in FIG. 3) in sidewall 351S. When a lip 387C on a drape management feature 387 is placed in opening 351B (which comprises part of the drape management alignment element), drape management feature 387 is properly mounted on surgical drape installation aid 350.

Figure 4:
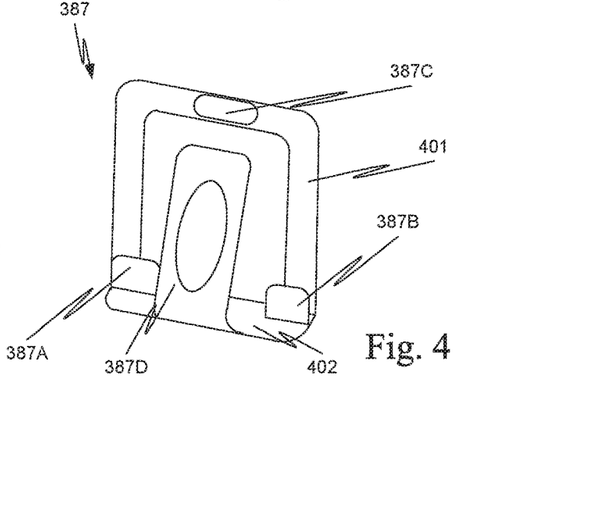
FIG. 4 illustrates an example of a drape management feature.

In this example, drape management feature 387 is implemented as a clamp 387 (FIG. 4). Clamp 387 is representative of each of the plurality of drape management features. Clamp 387 includes a frame 401, which is an upside down U-shape. Frame 401 extends vertically away from a base 402 of clamp 387. Lip 387C extends from one side of a leg of frame 401, a horizontal leg in this example, that is most removed from base 402. Lip 387C is shaped to fit in opening 351B.

Two tabs 387A and 387B also extend vertically away from base 402. Tabs 387A and 387B are separated from the vertical legs of frame 401 by a distance about equal to a thickness of sidewall 351S. This distance is large enough that sidewall 351S can be positioned between the vertical legs of frame 401 and tabs 387A and 387 and so the edge comprising first end 351E1 of sidewall 351S contacts base 402, but small enough that friction between inner surface 351SI of sidewall 351S and the vertical legs of frame 401 and friction between outer surface 351SO of sidewall 351S and tabs 387A and 387B help maintain clamp 387 attached to sidewall 351S. A sprung clip 387D also extends in a vertical direction from base 402. In one aspect, clamp 387 is made from a polycarbonate, but other materials could be used so long as clamp 387 functions as described herein.

While in this example the plurality of drape management features are mounted on body 351 of drape management aid 350, this is illustrative only and is not intended to be limiting. In another aspect, the plurality of drape management features are formed as part of body 351. In yet another aspect, plurality of drape management features are welded or heat staked to body 351, and so become part of body 351. Alternatively, the plurality of drape management features could be tape or features molded into drape management aid 350.

In this aspect, surgical drape installation aide 350 also includes a bag 352 with an open end attached to inner surface 351SI of sidewall 351S. For example, the open end of bag 352 is attached to inner surface 351SI using double-sided tape 389. The length of bag 352 that extends below the edge comprising first end 351E1 of sidewall 351S is selected so that surgical drape installation package 170 can be mounted on entry guide manipulator assembly platform 132 without any part of bag 352 contacting the floor, so that the plurality of boots do not have to be mounted on the plurality of surgical instrument manipulator assemblies at the time of mounting package 170, and without any part of bag 352 swinging and contacting an entry guide manipulator link. In one aspect, the bag is a polyethylene bag, but there are no special requirements for the material of bag 352.

Figure 5:
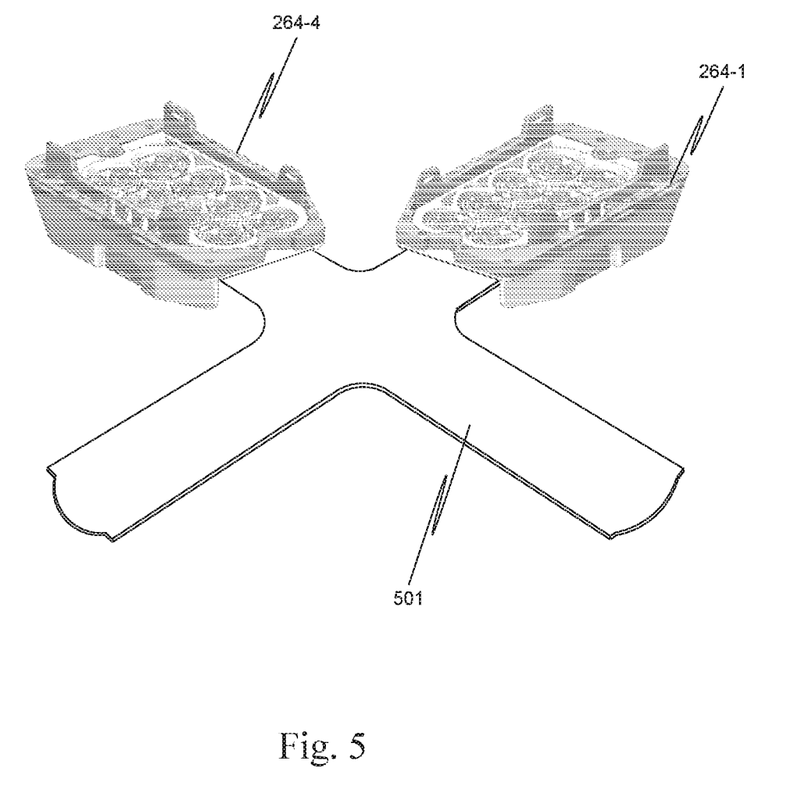
FIG. 5 illustrates a sterile adapter retaining device.

To mount surgical drape in surgical drape installation aid 350, sometimes referred to as aid 350, aid 350 is placed on a flat surface with bag 352 folded inside sidewall 351S. In this example, each of the plurality of sterile adapters 264-1 to 264-4 (sterile adapters 264-3 and 264-4 are not visible) of surgical drape 160 are mounted on a sterile adapter retaining device 501. In this example, sterile adapter retaining device 501 has a cross shape with four legs spaced equidistance apart. A leg of retaining device 501 fits in a corresponding sterile adapter. For clarity, the boots and plurality of drape sleeves of surgical drape 160 that are attached to the sterile adapters are not shown. Also, FIG. 5 shows an intermediate state were only two of the four sterile adapters are mounted on sterile adapter retaining device 501.

After all the sterile adapters are mounted on sterile adapter retaining device 501, the plurality of sterile adaptors, plurality of boots 263-1 to 263-4, and plurality of drape sleeves 262-1 to 262-4 are placed in the interior volume of body 351 inside of bag 352. Specifically, second portion 262 of surgical drape 160 is placed in the interior volume of body 351 inside of bag 352 (FIG. 6).

Figure 7:
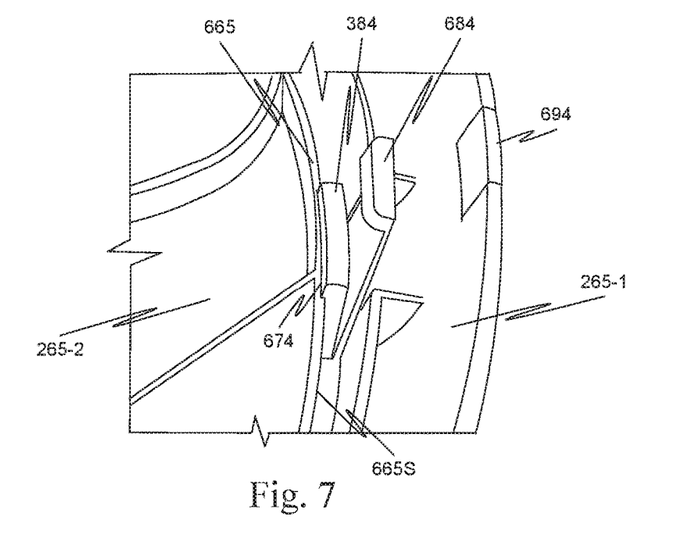
FIG. 7 is an illustration of the attachment of the rotatable seal to the surgical drape installation aid.

Next rotatable seal 265 is mounted on plurality of rotatable seal interface elements 380. FIG. 7 illustrates in more detail an example of one interface between rotatable seal 265 and one of the rotatable seal interface elements in plurality 380. In FIG. 7, rotatable seal interface element 384 is used as representative of each of the rotatable seal interface elements in plurality 380 illustrated in FIG. 3. In this example, rotatable seal 265 is a labyrinth seal, as described above. The labyrinth seal includes a roll cover portion 265-1 and a base comb portion 265-2. Base comb portion 265-2 is rotatable within and relative to roll cover portion 265-1.

In the example of FIG. 6, base comb portion 265-2 is a disc 665 with ribs that form a plurality of wedge-shaped "frames" with apertures, each of the frames sized to circumscribe an instrument manipulator. A proximal end of each of the plurality of drape sleeves is coupled to a different one of the frames of base comb portion 265-2.

When the labyrinth seal is mounted on body 351, a latch 684 of base comb portion 265-2 is aligned with rotatable seal interface element 384 of surgical drape installation aid 350, and the labyrinth seal is mounted on the edge comprising second end 351E2 on sidewall 351S. Rotatable seal interface element 384 protrudes between latch 684 of roll cover portion 265-1 and an outer circumferential edge 665S of disc 665. Outer circumferential edge 665S includes a notch 674, which locks base comb portion 265-2 in place, and so prevents rotation of base comb portion 265-2 until after surgical drape installation aide 350 is removed.

Base comb portion 265-2 includes a plurality of pins 686 that extend from the proximal end of disc 665 in the proximal direction. Each of plurality of pins 686 must be mounted in a matching receptacle in the distal face of entry guide manipulator assembly 133 so the base comb portion 265-2 rotates when entry guide manipulator assembly 133 rotates the plurality of surgical instrument manipulator assemblies. The locking mechanism shown in FIGS. 3, 7, and 8, which holds base comb portion 256-2 in the proper orientation relative to plurality of latches 681 to 684, assures that when rotatable seal 265 is mounted using surgical drape installation package 170, each of plurality of pins 686 is aligned with the corresponding receptacle.

Thus, initially, the plurality of sleeves and boots are placed inside body 351, and base comb portion 262-2 and roll cover portion 265-1 are mounted on body 351. Next, first drape portion 261 is accordion folded and accordion folded first drape portion 261 is held in place around outer surface 351SO by the plurality of drape management features. FIG. 6 shows surgical drape 160 mounted in surgical drape installation aide 350 to form one surgical drape installation package 670, which is one example of surgical drape installation package 170.

To assist a user in orientating surgical drape installation package 670 for mounting on a patient side support system 910 (FIG. 9A) of a surgical system, several orientation features are included in surgical drape installation package 670. In one aspect, a disc of roll cover portion 265-1 has a cut-out portion 666 that is shaped to fit about part of a fourth link 919 of an entry guide manipulator 930 (also called "manipulator arm assembly 930"). Cut-out portion 666 indicates to the user which part of surgical drape installation package 670 should be orientated toward link 919, and so provides gross orientation alignment guidance. Finer orientation alignment guidance is provided by a plurality of orientations markers 691 to 694. Each of plurality of orientations markers 691 to 694 is aligned with a corresponding latch in plurality of latches 681 to 684. In one aspects, one or more orientation markers are used, e.g., less than one per latch.

In one aspect, orientations markers 691 to 694 are colored pieces that are mounted in cut-outs in the disc of roll cover portion 265-1. Alternatively, the disc of roll cover portion 265-1 can be marked in other ways on its outer circumferential surface to indicate the location of a latch or the locations of latches, e.g., a hole, a notch in the edge surface, indentations in the edge surface, colored dots, etc. Plurality of orientations markers 691 to 694 permit a user to align package 670 with entry guide manipulator assembly platform 932 to that each of the plurality of latches is aligned with a corresponding receptacle in entry guide manipulator assembly platform 932. The proper alignment of the parts of the rotatable seal with the features of the patient side support system when package 670 is mounted speeds up the draping process, because it is not necessary to manually align parts of the rotatable seal with corresponding parts of the patient side support system 910 (FIG. 9A).

Element 660 is a poly-tie that is attached to the circumference of outside surface of first drape portion 261. Element 660 prevents the first drape portion 261 from unfolding while surgical drape installation package 670 is attached to link 919. Element 660 is removed after surgical drape installation package 670 is attached to patient side support system 990 so that first drape portion 261 can be pulled over the links of the patient side support system 990.

Surgical drape installation package 670 can be picked up in one of two ways. In a first way, the user grasps package 670 and holds bag 352 in the collapsed state as package 670 is positioned for mounting. See FIG. 1. In a second way, the user grasps the side of package 670, and as package 670 is lifted, bag 352 goes from a collapsed stated to an extended state. See FIG. 8. Plurality of boots 263-1 to 263-4 remain in bag 352 as package 670 is lifted and so are no longer in the interior volume of body 351.

Figure 9A:
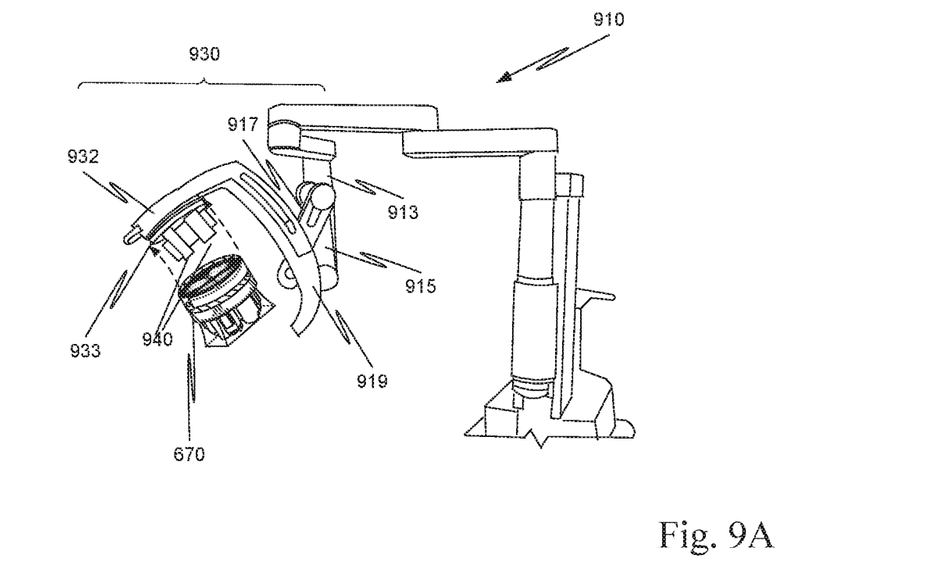
FIGS. 9A and 9B illustrate mounting the surgical drape installation package on a patient side support system.

In FIG. 9A, patient side support system 910 is similar to patient side support system 110 in FIG. 1. In particular, actively controlled manipulator arm assembly 130 is equivalent to actively controlled manipulator arm assembly 930 so that links 113, 115, 117, 119, entry guide manipulator assembly 133, and plurality of surgical instrument manipulator assemblies 140 are equivalent to links 913, 915, 917, 919, entry guide manipulator assembly 933, and plurality of surgical instrument manipulator assemblies 940, respectively. Thus, the description associated with FIG. 1 for these elements is not repeated here for the corresponding elements in FIG. 9A, but is incorporated herein by reference.

Figure 8:
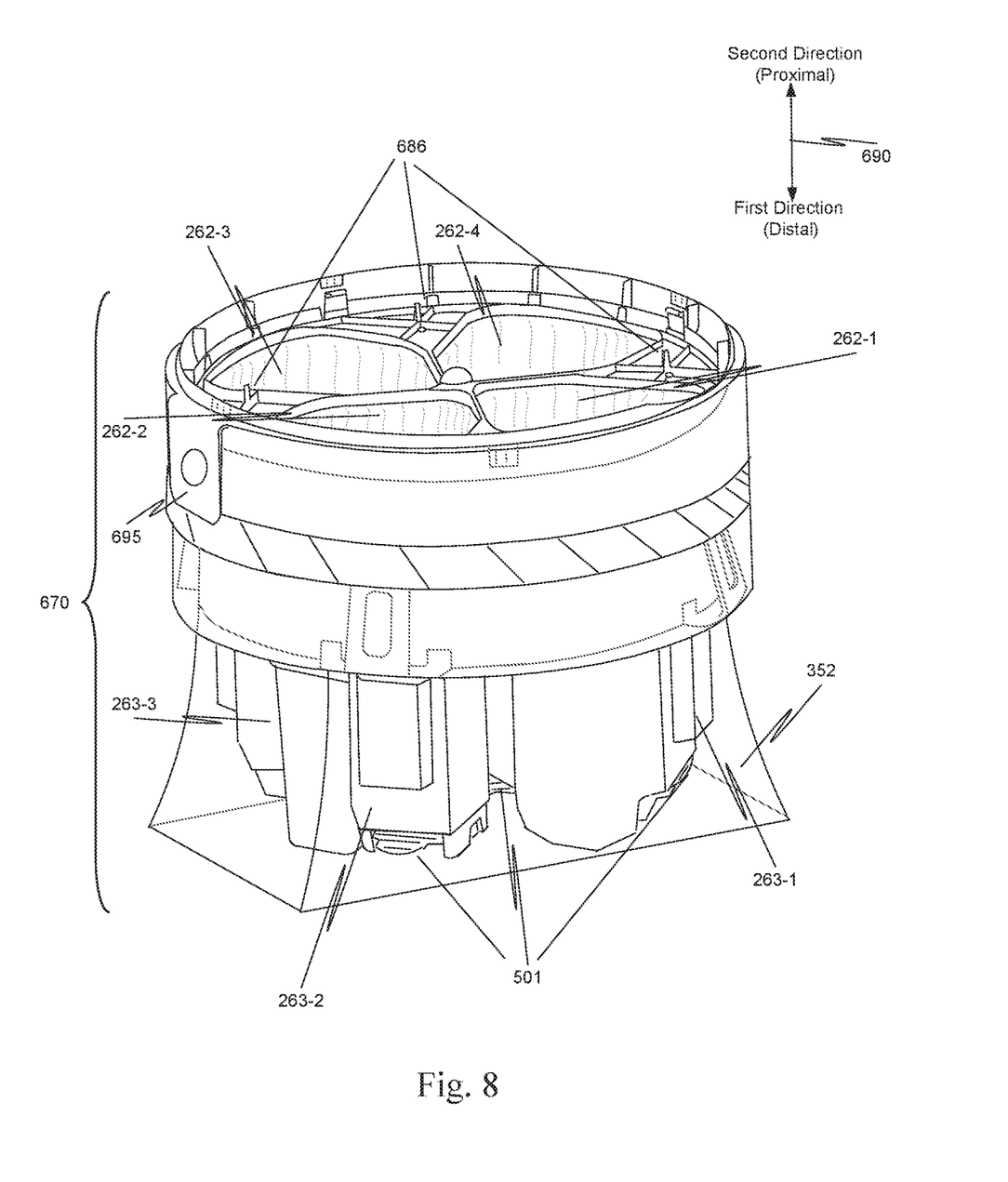
FIG. 8 is an illustration of the surgical drape installation package when the package is lifted.
Figure 9B:
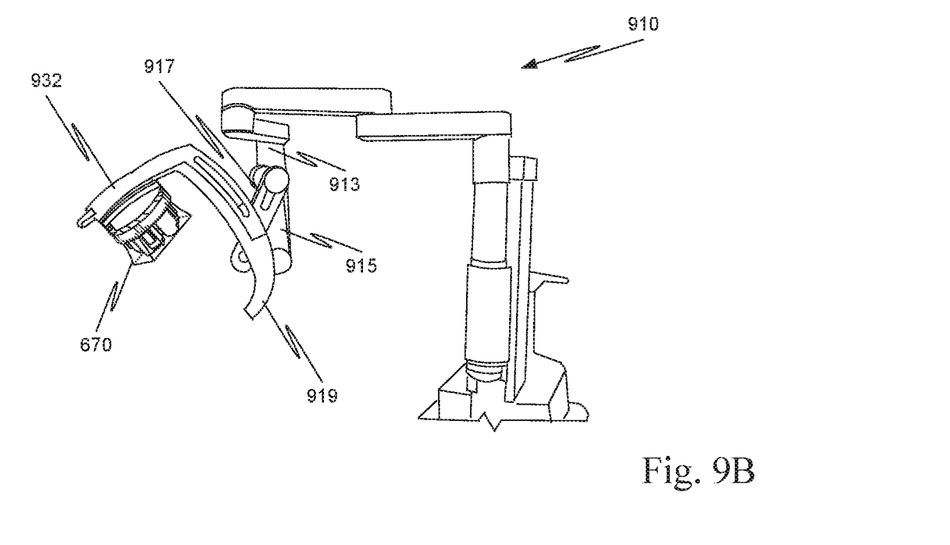

FIG. 9A illustrates package 670 (FIG. 8) being moved into position for mounting on platform 932 on one end of link 919. FIG. 9B shows package 670 mounted on platform 932. In particular, each of the plurality of latches of rotatable seal 265 has been engaged in a corresponding latch receptacle in platform 932.

First portion 261 of drape 160 is unfolded from package 670 and worked around at least links 919, 917, 915, and 913, and then is affixed to link 913. This process is difficult for one person to perform due to the physical size of patient side support system 910. Thus, a sterile person that deploys first portion 261 of drape 160 is assisted by a second person, who need not be sterile. As shown in FIGS. 6 and 8, the inside of first portion 261 of drape 160 includes at least one assistant's handle 695. The non-sterile person grasps assistant's handle 695 and helps in working the side of the drape opposite to the sterile person around the links. Since assistant's handle 695 is on the interior surgical drape, the non-sterile person grasping and manipulating the drape does not affect the sterile outside portion of the surgical drape. In one aspect, first portion 261 of drape 160 includes a plurality of assistant's handles.

After first portion 261 of surgical drape 160 is deployed, surgical drape installation aide 350 is pulled from rotatable seal 265, and each of plurality of sleeves 261-1 to 261-4 extends to its maximum length. Since sterile adapters 264-1 to 264-4 are coupled together by sterile adapter retaining device 501, a sleeve, its boot and sterile adapter are inhibited from swinging and contacting a non-sterile surface as surgical drape installation aide 350 is removed.

Figure 10:
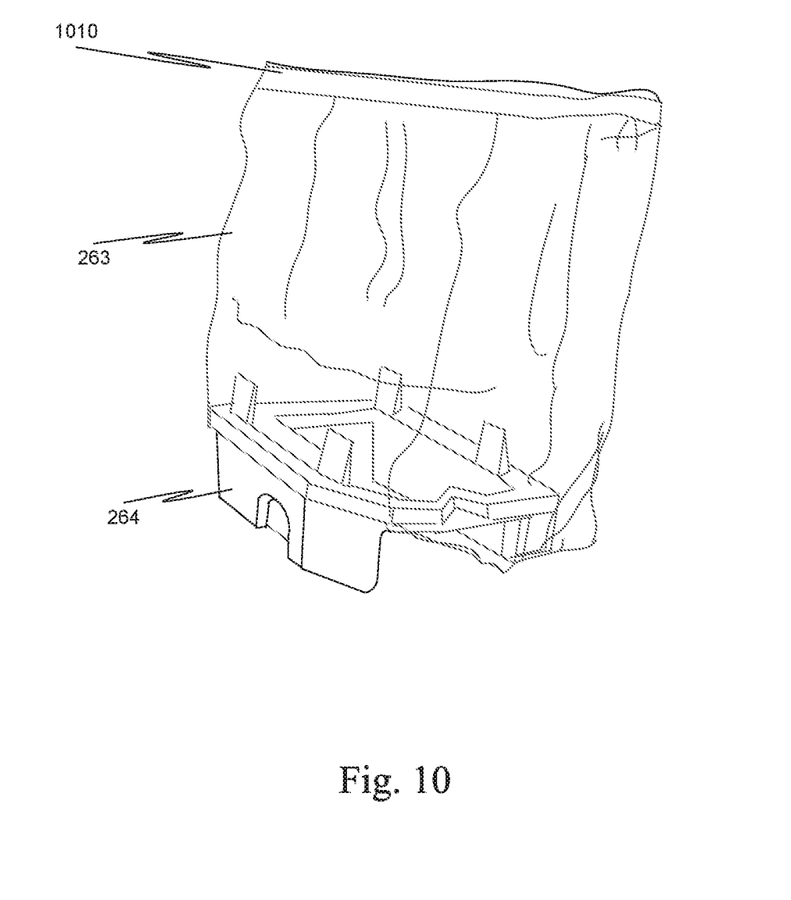
FIG. 10 is a more detailed illustration of a boot of a surgical drape.

FIG. 10 is an illustration of a representative boot 263 of the plurality of boots and the corresponding sterile adapter 264 in the plurality of sterile adapters. In one aspect, boot 263 is made from low-density polyethylene (LDPE) and is shaped to fit around an instrument manipulator. Boot 263 is affixed to sterile adapter 264 between parts of sterile adapter 264. Sterile adapter 264 is configured to mate a surgical instrument manipulator assembly. Band 1010 at the proximal end of boot 263 is two-sided tape, which is used to attach a drape sleeve to boot 263.

As used herein, "first," "second," "third," etc. are adjectives used to distinguish between different components or elements. Thus, "first," "second," and "third" are not intended to imply any ordering of the components or elements or to imply any total number of components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures were turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

Embodiments described above illustrate but do not limit the disclosure. It should also be understood that numerous modifications and variations are possible in accordance with the principles of the present disclosure. For example, in many aspects the devices described herein are used as single-port devices; i.e., all components necessary to complete a surgical procedure enter the body via a single entry port. In some aspects, however, multiple devices and ports may be used.

We claim:

1. A surgical drape installation aid comprising:
a body comprising a sidewall and a plurality of rotatable seal interface elements, the sidewall having a first end and a second end, the first end of the sidewall bounding a first open end of the body, the second end of the sidewall bounding a second open end of the body, each of the plurality of rotatable seal interface elements extending from the second end of the sidewall, and the sidewall bounding an interior volume of the body.

2. The surgical drape installation aid of claim 1, further comprising:
a bag having an open end, the open end of the bag being fixedly attached to a first surface of the sidewall between the first end of the sidewall and the second end of the sidewall, the bag being configured to extend from the first end of the sidewall.

3. The surgical drape installation aid of claim 2, further comprising:
a plurality of surgical drape management features, each of the plurality of surgical drape management features being configured to hold a portion of a surgical drape against a second surface of the sidewall, the first surface of the sidewall and the second surface of the sidewall being different surfaces.

4. The surgical drape installation aid of claim 1, further comprising:
a plurality of surgical drape management features, each of the plurality of surgical drape management features being configured to hold a portion of a surgical drape against a surface of the sidewall.

5. The surgical drape installation aid of claim 4, the plurality of surgical drape management features comprising a clamp attachable to the sidewall.

6. The surgical drape installation aid of claim 1, wherein the body comprises an open circular cylinder.

7. The surgical drape installation aid of claim 1, further comprising a sterile adapter retaining device.

8. A system comprising:
a surgical drape comprising a first portion and a second portion; and
a surgical drape installation aid comprising a body comprising a sidewall, the sidewall having a first end, a second end, an interior side surface, and an exterior side surface, the exterior side surface extending between the first end and the second end, the interior side surface extending between the first end and the second end, the first end of the sidewall bounding a first open end of the body, the second end of the sidewall bounding a second open end of the body, and the interior side surface of the sidewall bounding an interior volume of the body;
wherein the second portion of the surgical drape is positioned in the interior volume of the body, and wherein at least part of the first portion of the surgical drape is mounted on the exterior side surface of the body.

9. The system of claim 8,
wherein the surgical drape further comprises a rotatable seal comprising a stationary seal portion and a rotatable seal portion, the rotatable seal portion being configured to rotate relative to the stationary seal portion, the first portion of the surgical drape being fixed to the stationary seal portion, and the second portion of the surgical drape being fixed to the rotatable seal portion;
wherein the surgical drape installation aid further comprises a plurality of rotatable seal interface elements, each of the plurality of rotatable seal interface elements extending from the second end of the sidewall; and
wherein the plurality of rotatable seal interface elements is engaged with the rotatable seal.

10. The system of claim 9, wherein the wherein the rotatable seal comprises a labyrinth seal.

11. The system of claim 8, the surgical drape installation aid comprising:
a bag having an open end, the open end of the bag being fixedly attached to the interior side surface of the sidewall between the first end of the sidewall and the second end of the sidewall, the bag being configured to extend from the first end of the sidewall.

12. The system of claim 11, the surgical drape installation aid further comprising:
a plurality of surgical drape management features, each of the plurality of surgical drape management features being configured to hold the part of the first portion of the surgical drape against the exterior side surface of the sidewall.

13. The system of claim 8, the surgical drape installation aid further comprising:
a plurality of surgical drape management features, each of the plurality of surgical drape management features being configured to hold the part of the first portion of the surgical drape against the exterior side surface of the sidewall.

14. The system of claim 13, the plurality of surgical drape management features comprising a clamp attachable to the sidewall.

15. The system of claim 8, wherein the body of the surgical drape installation aid comprises an open circular cylinder.

16. The system of claim 8, the surgical drape installation aid further comprising a sterile adapter retaining device.

17. The system of claim 8, wherein the first portion of the surgical drape comprises at least one handle configured to be grasped by a user.

18. A method comprising:
placing a second portion of a surgical drape in an interior volume of a body of a surgical drape installation aid, the body comprising a sidewall, the sidewall having a first end, a second end, an interior side surface, and an exterior side surface, the exterior side surface extending between the first end and the second end, the interior side surface extending between the first end and the second end, the first end of the sidewall bounding a first open end of the body, the second end of the sidewall bounding a second open end of the body, and the interior side surface of the sidewall bounding the interior volume; and
mounting a first portion of the surgical drape on the exterior side surface of the body.

19. The method of claim 18, the first portion and the second portion of the surgical drape being attached to a rotatable seal, the mounting the first portion further comprising:
mounting the rotatable seal on a plurality of rotatable seal interface elements, each of the plurality of rotatable seal interface elements extending from the second end of the sidewall.

20. The method of claim 18, wherein mounting the first portion of the surgical drape on the exterior side surface of the body comprises retaining the first portion of the surgical drape on the exterior side surface of the body with a plurality of drape management features.

* * * * *